United States Patent [19]
Delente

[11] Patent Number: 5,432,094
[45] Date of Patent: * Jul. 11, 1995

[54] APPARATUS AND METHOD FOR COLLECTING, DETECTING AND INDICATING TRUE ALVEOLAR BREATH COLLECTIONS

[75] Inventor: Jacques J. Delente, Kensington, Md.

[73] Assignee: Martek Biosciences Corporation, Columbia, Md.

[*] Notice: The portion of the term of this patent subsequent to May 18, 2010 has been disclaimed.

[21] Appl. No.: 279,073

[22] Filed: Jul. 22, 1994

Related U.S. Application Data

[63] Continuation of Ser. No. 21,544, Feb. 24, 1993, abandoned.

[51] Int. Cl.$^6$ .................. G01N 33/00; G01N 7/00; A61B 5/08
[52] U.S. Cl. .................... 436/127; 436/167; 128/730; 422/84; 422/85; 422/61; 422/102; 73/863.71
[58] Field of Search .......... 422/84, 83, 85, 61, 422/102; 436/41, 127, 167; 128/719, 727, 728, 730; 73/863.71, 863.72, 864.55, 865,63

[56] References Cited

U.S. PATENT DOCUMENTS

| | | | |
|---|---|---|---|
| 3,544,273 | 12/1970 | McConnaughey | 128/719 |
| 3,734,692 | 3/1973 | Lucker et al. | 128/719 |
| 3,777,571 | 12/1973 | Jaeger | 128/719 |
| 3,858,573 | 1/1975 | Ryan et al. | 128/719 |
| 4,201,080 | 5/1980 | Slepak et al. | 73/73 |
| 4,274,425 | 6/1981 | Lutz et al. | 422/84 |
| 4,370,152 | 1/1983 | Luper | 55/281 |
| 4,402,911 | 9/1983 | Walters | 422/102 |
| 4,579,826 | 4/1986 | Botton et al. | 128/719 |
| 4,624,929 | 11/1986 | Ullman | 436/165 |
| 4,644,807 | 1/1987 | Mar | 73/864.62 |
| 4,740,475 | 4/1988 | Paul | 436/165 |
| 4,947,861 | 9/1990 | Hamilton | 128/719 |
| 5,211,181 | 5/1993 | Delente | 128/730 |
| 5,322,161 | 6/1994 | Shichman et al. | 206/204 |

OTHER PUBLICATIONS

Asami, Taiichi; "Determination of Minute Quantites of Water in Gas or Liquids by Cobaltous Chloride Indicators"; Anal. Chem; 40(3), 648–50, 1968.

Primary Examiner—Robert J. Warden
Assistant Examiner—Christopher Y. Kim
Attorney, Agent, or Firm—Rothwell, Figg, Ernst & Kurz

[57] ABSTRACT

A simplified, user-friendly method and apparatus for collecting and storing a human breath sample and for detecting and indicating whether the stored breath sample is a true alveolar sample. The invention includes in one embodiment thereof a preferably transparent container and a breath delivery device for directing a subject's breath into the container. A closure device is provided for accommodating the insertion of the breath delivery device into the container and for substantially sealing the container. A detector is provided for being positioned within the sealed container for detecting and indicating to an observer whether the breath sample stored in the container is a true alveolar sample.

18 Claims, 3 Drawing Sheets

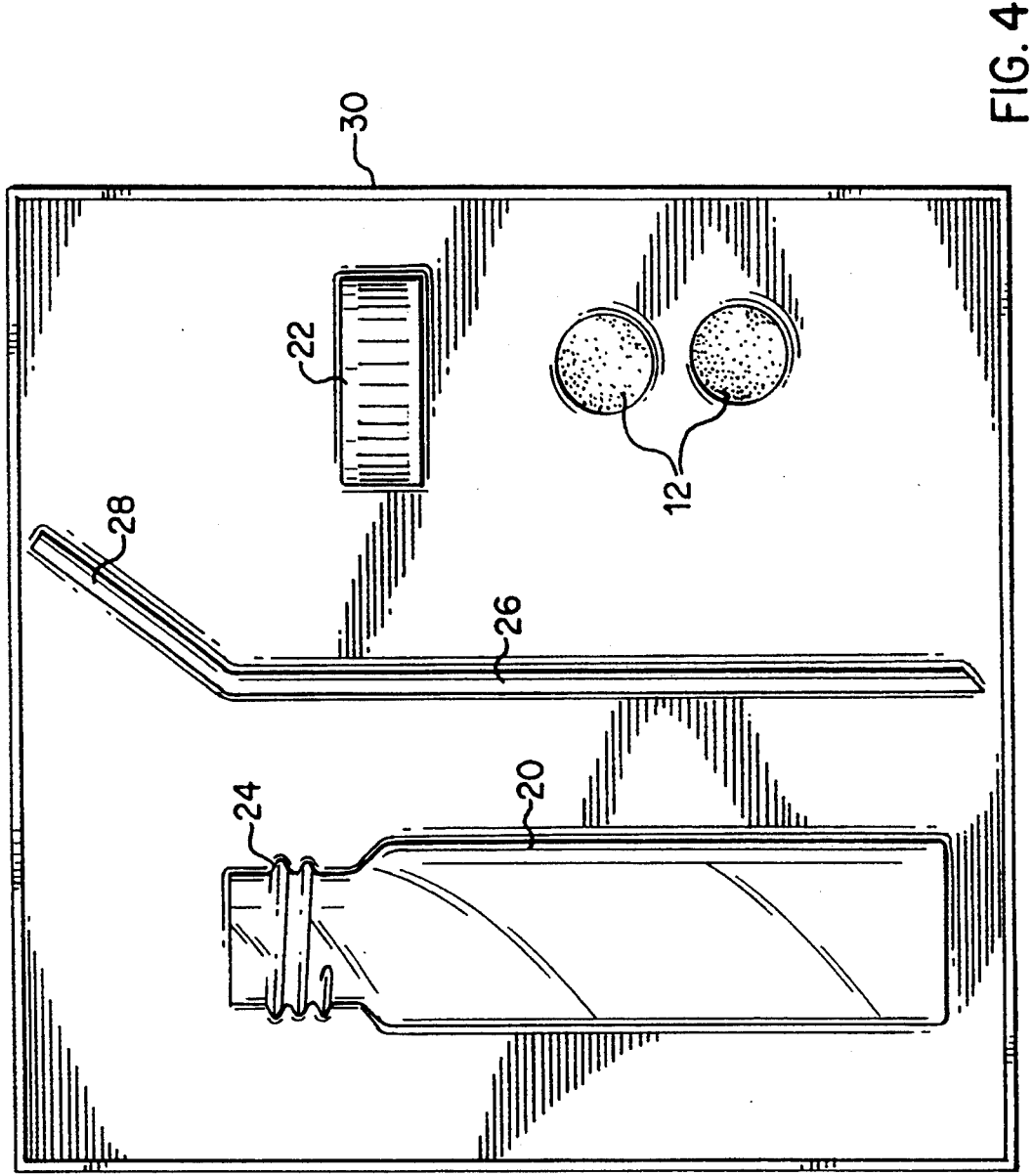

APPARATUS AND METHOD FOR COLLECTING, DETECTING AND INDICATING TRUE ALVEOLAR BREATH COLLECTIONS

This is a continuation of application Ser. No. 08/021,544, filed Feb. 24, 1993, abandoned.

BACKGROUND OF THE INVENTION

1. Field of the Invention

This invention relates generally to a method and apparatus for collecting, detecting and indicating true alveolar breath samples from humans and, in particular, is directed to an uncomplicated, user-friendly and relatively inexpensive apparatus and method for collecting such breath samples and detecting, indicating and thereby assuring that they consist primarily of alveolar gas as expelled from the pockets of the lungs.

1. Description of the Prior Art

Certain diagnostic techniques require analysis of the breath of a human subject to determine whether the breath contains a particular chemical compound, such as ethyl alcohol, carbon dioxide or ammonia, or a non-chemical, such as a particular microorganism. Determining the constituent components of the breath is best accomplished by analyzing the alveolar gas, that is the portion of the exhaled breath which is expelled from the air pockets of the lungs. In exhalation, as the lungs contract, breath contained in the mouth, throat and bronchials is necessarily exhaled first, followed by the breath contained in the alveoli of the lungs. Since it is at the alveoli where the exchange of substances between breath and blood ultimately occurs, the concentration of gaseous or vaporous constituents in the alveoli corresponds more closely to the concentration of substances dissolved in the blood. Thus, if a sample of breath is to be analyzed for the presence of constituents which may be present in the blood, the sample of breath analyzed must be at least primarily alveolar gas.

In order to make sure that a subject has expelled a full alveolar breath sample suitable for purposes of analysis, the apparatus and methods of the prior art utilize multiple collector configurations, with the alveolar portion of the expelled breath being collected in a second container. After collection of the alveolar portion of the breath sample in the second container, the alveolar breath present in the second container is then removed by means of a syringe and transferred in an evacuated tube. Such prior art techniques are awkward, difficult to use and risk prone (e.g., the syringes can be tempting to drug addicts).

More specifically, the equipment commonly used for collecting alveolar breath samples consists of bags, valves, syringe and needles and evacuated containers such as used for blood samples. These devices are expensive and complex which makes them very difficult for a patient to use. For example, U.S. Pat. No. 3,734,692 discloses an alveolar breath sampling apparatus utilizing a complicated compartmentalized bag having first and second inflatable regions. A dual channeled delivery port is constructed into the apparatus and communicates with both regions. The breath sample is collected by breathing into the delivery port resulting in the sequential collection in each region. This device is unnecessarily complex and expensive to construct.

In another known arrangement, the alveolar air portion of a person's breath is separated in response to the temperature of the conveyed air. For example, U.S. Pat. No. 4,248,245 discloses a method and device for separating alveolar air which includes conveying the exhaled air through a conduit and continuously monitoring the temperature of the conveyed air. When the variation in measured temperature drops below a threshold value, the air is directed into a measuring chamber. This device is also excessively complex and expensive to manufacture.

In still another prior art arrangement, two separate collection bags are used interconnected by a conduit. For example, in U.S. Pat. No. 3,544,273, a first collection bag and a second collection bag are connected by a T-shaped conduit having one branch formed into a mouth piece. The breath sample is collected by inflating the first bag with the initial breath portion and filling the second bag will the alveolar air. The second bag is sealed by using a valve structure. The complexity of these devices and resultant difficulty individual users have in operating them and the absence of a positive means for detecting and indicating the presence of a full alveolar breath sample have often resulted in less than accurate measurements. In addition, such prior art systems are intimidating to the user and difficult to use in any event and thus are not as widely used as considered medically prudent for early diagnostic purposes.

In addition, because of the high cost of such prior art apparatus, the economics of use often dictate that the apparatus be reused instead of being discarded after initial use. It is a common practice, therefore, to sterilize and reuse such apparatus for other patients after each use. Because sterilization may not always be fully effective and because contamination of the apparatus may occur in any event prior to the next use, patients subsequently using the apparatus are exposed to additional risks.

SUMMARY OF THE INVENTION

Accordingly, the present invention provides, in one embodiment thereof, an inexpensive and user-friendly method and apparatus for collecting in a single container and accurately detecting and indicating the presence of a full alveolar human breath sample. In a preferred embodiment, the apparatus of the present invention utilizes a single chamber capable of receiving and collecting alveolar breath and having positioned therein a detector element which detects and visually indicates whether the breath sample which has been collected in the container is a true alveolar sample suitable for accurate diagnostic purposes.

It has been determined, in accordance with the implementation of the present invention, that air taken into the human respiratory system reaches different levels of moisture content depending upon its location within the respiratory system during the breath inhaling and exhaling cycle. That is, air which is deeply inhaled into the lungs and which participates fully in the oxygen-carbon dioxide exchange process reaches a higher level of moisture content than air which remains in the upper part of the system (generally referred to as "dead space air").

In one preferred embodiment of the invention, the detector comprises a material positioned in the chamber containing the breath sample and which responds to the moisture content of the breath sample, that is, the relative humidity of the sample, and determines from that parameter whether or not the sample is a true alveolar sample. In one embodiment, the moisture sensitive material of the detector is a material which changes color as it absorbs moisture from the breath sample in the container. Thus, after the sample is expelled into the container and a short period of time is allowed to expire in which the detector reaches an equilibrium condition relative to moisture content of the breath sample, the color of the detector indicates whether the sample is a true alveolar sample.

In the practice of the method of the present invention in one embodiment thereof, the detector is positioned within the interior of a container in which the breath sample is to be collected and stored. The sample is then taken by a human subject expelling a breath within the container and the container is closed to store the sample in the container along with the detector. The detector then functions within the closed container to detect the alveolar quality of the sample and to indicate the detected condition of the sample to an observer.

The components of the breath sample and storing apparatus of the present invention may also be provided in convenient kit form so that the user may position the detector within the container and use the apparatus and perform the steps of taking and storing the sample in accordance with the method of the invention. The detector thereafter functions automatically to detect and indicate to the subject and thereafter to diagnostic personnel the condition of the sample stored in the container.

In one embodiment, the detector is in the form of paper based element which has been impregnated with a substance which is sensitive to the relative humidity of the sample stored within the device. The detector reacts by changing color in response to the level of the relative humidity of the breath sample to indicate whether the sample is a true alveolar sample. The detector is reliable and, at the same time, is inexpensive and can thus be readily discarded and a new sample substituted after each use.

BRIEF DESCRIPTION OF THE DRAWINGS

FIG. 4 is an illustration of a kit containing the elements of the embodiment shown in FIGS. 3 and 3A.

DETAILED DESCRIPTION OF THE INVENTION

Figure 1:
FIG. 1 is a front elevational view of a breath collection apparatus embodying the present invention.

Referring now to FIG. 1, there is shown a breath collection apparatus 10 including an elongated, hollow, rigid tubular container 1 having an elongated, hollow chamber 2 therein. The breath collection apparatus shown in FIG. 1 is of the general type disclosed in copending U.S. patent application Ser. No. 07/702,022, entitled APPARATUS AND METHOD FOR COLLECTING HUMAN BREATH SAMPLES, filed May 17, 1991 in the name of Jacques J. Delente and assigned to the same assignee as the present application, the disclosure of which application is incorporated herein by reference.

The elongated container 1 has a closed end 3 and an opposite end thereof having an inlet portion 4 forming an opening to the interior of chamber 2. The elongated tubular container can be any suitable closeable container. In a preferred embodiment, the tubular container is a common commercially available vial or test tube which forms the elongated, hollow chamber 2 which has a length substantially greater than its diameter. As will be explained further below, the elongated container 1 is preferably formed of a transparent material.

The breath collection apparatus of FIG. 1 includes an elongated, hollow breath delivery means 6 for delivering a breath sample from a subject's mouth into the chamber 2. The breath delivery means can be any suitable, preferably hollow, device which will facilitate directing a subject's exhaled breath into the container's interior chamber. In a preferred embodiment, the breath delivery means is a common commercially available plastic or glass straw.

The embodiment of FIG. 1 also includes closure means 5 for closing and substantially sealing the inlet portion 4 of the elongated container 1. The closure means 5 operates in at least two different positions. In a first position, the closure means accommodates the insertion of the breath delivery means into the container's interior chamber 2 as is illustrated in FIG. 1. In a second position, the closure means substantially seals the inlet portion 4 of the container 1. In the embodiment shown in FIG. 1, the closure means is placed in the second position to seal the inlet portion 4 after the removal of the delivery means 6.

The closure means 5 is adapted to removably seal the inlet portion of the elongated container 1 and to accommodate the insertion of the delivery means 6 in a manner such that the opening into the chamber 2 is at least partially covered during the use of the delivery means 6. In a preferred embodiment, the closure means 5 is formed of a resilient material, such as butyl rubber, and is shaped in the form of a disk 5 with one or more projecting blades 8 extending therefrom. The blades 8 provide means for facilitating positioning of the closure means into the first and second positions and for accommodating the insertion of the breath delivery means 6.

As disclosed in the above referenced copending patent application, the volume of elongated container 1 is substantially smaller than the volume of a normal exhaled breath. This comparatively small volume is provided so that as the subject exhales his or her breath through the breath delivery means, the initial portion of the expiration is purged from the interior chamber 2 through the inlet portion 4. Near the end of expiration, substantially only the alveolar air will remain which is then sealed in the container by closure means 5.

The further details of the breath collection apparatus 10 described thus far are given in the aforementioned patent application Ser. No. 07/702,022.

One of the difficulties associated with breath collection apparatus of the prior art has been the inability to determine whether or not the sample stored in the sample chamber, such as in the sample chamber 2, is in fact a true alveolar sample, that is a sample of breath which has been fully exposed by deep inhalation to the oxygen-carbon exchange reaction of the lungs. This is very difficult to determine by attempting to measure the chemical constituents of the sample itself because such a procedure interferes with the diagnostic process and does not yield an accurate determination of the alveolar quality of the breath sample in any event.

Pursuant to the present invention, it has been determined that the sensing of the alveolar condition of the breath sample can be effectively carried out by sensing the moisture content of the sample stored within the chamber 2. In this respect, it has been determined that air taken into the human respiratory system reaches different levels of moisture content depending upon its location within the respiratory system during the breath inhaling and exhaling cycle. That is, air which is deeply inhaled into the lungs and which participates fully in the oxygen-carbon dioxide exchange process (referred to herein as a "true alveolar sample") reaches a higher level of moisture content than air which remains in the upper part of the system (generally referred to as "dead space air").

Accordingly, the present invention provides detecting and indicating means for detecting the moisture content of the stored breath sample within the closed container and indicating to an observer, based on such detection, whether or not the stored sample is in fact a true alveolar sample.

Figure 2:
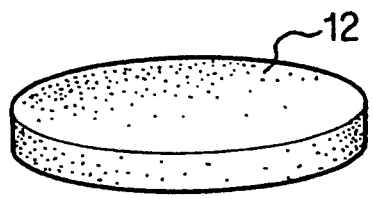
FIG. 2 is an enlarged perspective view of the detector and indicator means of the embodiment of FIG. 1.

Positioned within the chamber 2 is a detector and indicator element 12, which is illustrated in further detail in the enlarged perspective view of FIG. 2. The detector and indicator element 12 is preferably formed of a blotting paper or fibrous cardboard material in which the paper base is an ashless paper without significant mineral content. Such paper material is itself well known in the art.

The paper base material of the detector and indicator element 12 is impregnated with a material of a composition which is sensitive to the moisture content of the surrounding environment in which it is positioned. One such moisture sensitive composition, which is a preferred composition for the purposes of the present invention, is cobalt chloride of the chemical composition $CoCl_2$.

The cobalt chloride is impregnated in the paper base of the element 12 by first dissolving the cobalt chloride in a solvent, such as water, and then soaking the element 12 in the cobalt chloride solution and later evaporating the solvent. Cobalt chloride impregnated material suitable for use in the present invention is available as a commercial product which is used for the purpose of detecting the relative humidity of ambient air. Such a commercial product is available, for example, from Humidial Corporation of Colton, Calif. under the trade name "Humidial".

The detecting and indicating element 12 is formed in any suitable shape, such as in the form of a disk as shown in FIG. 2, for insertion and retention in the interior of the chamber 2. The element 12 is shown positioned in the bottom of the chamber 2 in the embodiment of FIG. 1.

In practicing the method of the present invention, the subject positions the element 12 within the chamber 2 of the container 1. Then, a breath sample is expelled by the subject into the chamber 2 and the chamber 2 is closed off by means of the closure means 5. The element 12 is thus exposed to the breath sample stored in the chamber 2 and to the moisture level which is present in the sample. After a short equilibration period, the moisture level of the fibrous base of the element 2 reaches the level of the stored sample and the cobalt chloride composition reaches the equilibrium moisture level of the sample. The cobalt chloride in the element 12 reacts to the moisture level by changing its color depending upon the relative humidity of the breath sample.

When exposed to relative low levels of moisture, such as, for example, a relative humidity in the range of 20% to 40% or so, the color of the sample is blue for the lower humidity levels and purple for the higher end of the range. At much higher levels of relative humidity, for example, in the range of 80% or so, the color of the element 12 becomes pink.

It has been determined that, in the case of a very short breath, or in the case of the "dead space air" portion of a breath which has not been deeply inhaled, and is thus not a true alveolar sample, the relative humidity of the sample is relatively low because moisture has not been deeply absorbed from the lung tissues. If such a sample is stored in the chamber 2 in the presence of the element 12, and allowed to reach an equilibrium condition, which has been found to occur in several minutes, the color of the element 12 will remain blue or, at best, a purple color. The blue or purple color of the element 12, as observed through the transparent wall of the container 1, thus indicates that the stored sample is not a true alveolar sample.

On the other hand, if the stored sample is a true alveolar sample, in which the relative humidity is in the range of 80% or so, the element 12 will turn pink in several minutes, indicating that the stored sample is in fact a true alveolar sample.

The detecting and indicating element 12 thus functions not only to detect the alveolar quality of the breath sample stored in the chamber 2, but it also gives a visual indication, which is visible to an observer looking though the transparent wall of the container 1, which allows the person taking the sample to immediately determine whether the sample taken is a true alveolar sample. The element 12 also retains its color corresponding to the relative humidity level in the chamber 2 and thus also allows laboratory personnel at the point of performing diagnostic tests to determine that the sample being analyzed is in fact a true alveolar sample. Further, it has been found that the cobalt chloride composition, with which the element 12 is impregnated, does not interact with the constituent elements of the stored breath sample, even under prolonged storage conditions.

In order to avoid any possible reaction between the base material of the element 12 and the constituent elements of the breath sample, the base material of the element 12 is selected to be as mineral free as possible and chemically inert with respect to the constituent elements of the breath sample which are to be detected for diagnostic purposes. As mentioned above, an ash free paper has been found to be satisfactory as the base material of the element 12 for the purposes of the present invention. Other materials which meet the same conditions will also be found to be satisfactory. The element 12 thus performs its functions without in any way interacting chemically or otherwise with the constituent elements of the breath sample itself and the integrity of the sample for diagnostic purposes is thus not compromised in any way. Further, the element 12 is inexpensive and nontoxic and can be discarded after use, thereby avoiding the need to sterilize any equipment for use by the next patient.

While the element 12 is shown in the embodiment presented herein in the form of a disk, it may be formed in any convenient shape to facilitate the ready observation thereof by an observer in order to determine the condition of the breath sample stored in the container 1.

The equipment of the breath sample and storing apparatus of the present invention may also be provided in convenient kit form so that the user may position the detector 12 within the container 1 and use the apparatus and perform the steps of taking and storing the sample in accordance with the method of the invention. After the taking and storage of the breath sample, the detector 12 thereafter functions automatically to detect and indicate to the subject and thereafter to diagnostic personnel the condition of the sample stored in the container.

Figures 3, 3A:
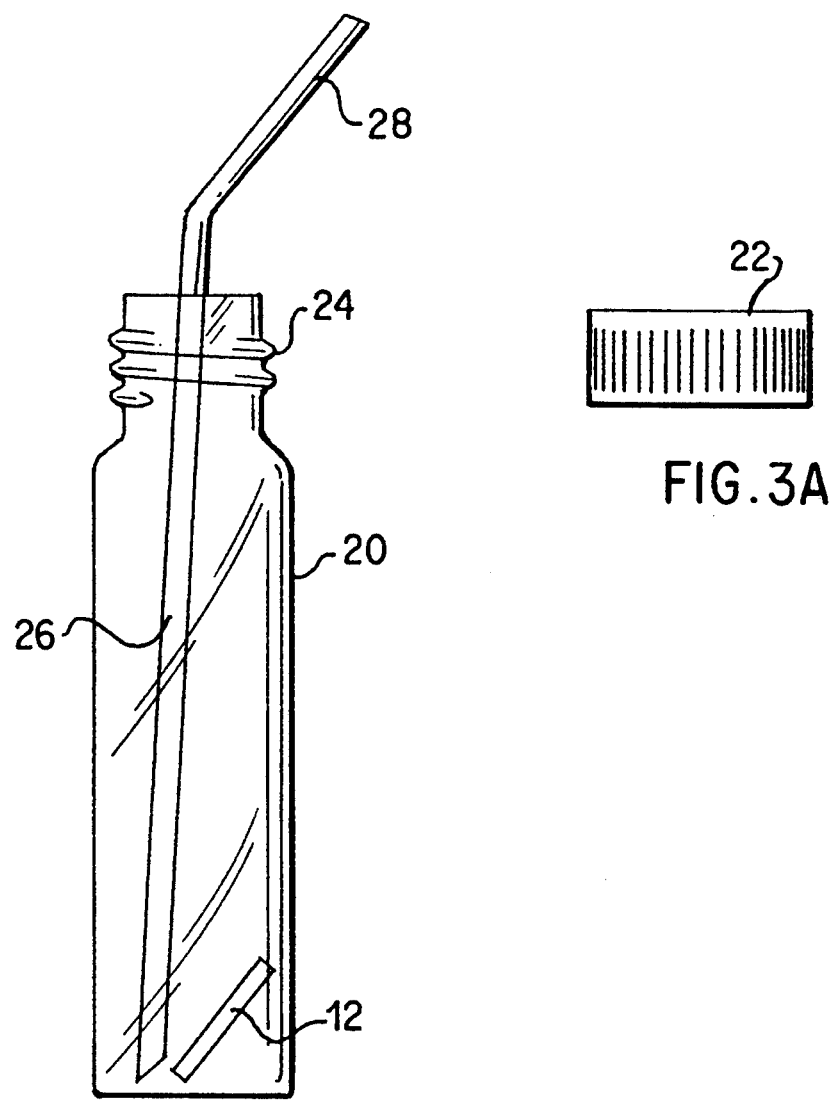
FIG. 3 is a front elevational view of another embodiment of the invention.
FIG. 3A is a side view of a closure means for the embodiment of FIG. 3.

The present invention is shown in a different embodiment in FIGS. 3 and 3A. In this embodiment, an elongated, hollow and preferably transparent container 20 is provided to receive and store the breath sample and is adapted to be closed and sealed by a cap 22, which is threaded internally to engage external threads 24 on the container 20. A breath delivery tube 26 is provided with a portion 28 adapted to engage the mouth of a subject to receive an expelled breath and store the same in the container 20. An alveolar condition detector 12 of the type described above is positioned in the container 20 as shown in FIG. 3. After the breath sample is expelled by the subject into the container 20, with the initial portion thereof being self-purged from the container to leave only the alveolar portion thereof, assuming the subject has used the equipment properly, the delivery tube 26 is withdrawn and the cap 22 is placed on the container to close and seal the same with the indicator 12 positioned therein as shown in FIG. 3. The operation of the embodiment of FIGS. 3 and 3A is otherwise the same as that of FIGS. 1 and 2.

The elements of the embodiment of FIGS. 3 and 3A are shown packaged in kit form in FIG. 4. The elements are arranged and secured in position in any suitable fashion in a box 30 which contains a breath collection and storage container 20, a breath delivery tube 26, a closure cap 22 and one or more disk shaped detector elements 12. Additional detectors 12 are preferably packaged in the kit so that a user may take and monitor several samples in the event an acceptable indication is not obtained from the initial sample or samples.

Although the invention has been shown and described in connection with particular embodiments in which it has been applied in connection with a particular type of breath collection apparatus, its application is not limited to the particular embodiments disclosed herein. The present invention may thus be employed with any type of breath collection equipment or apparatus. The detailed disclosure of the embodiments set forth herein is made for the purposes of setting forth a full and detailed disclosure of preferred embodiments of the present invention and is thus not to be interpreted or construed as limiting in any way the true scope of the present invention as set forth in the appended claims.

I claim:

1. A breath collection and storage apparatus comprising:
   collection means including a breath storage container for collecting and storing in said breath storage container a breath sample from a human subject; and
   detection means positioned within said breath storage container for detecting whether said stored breath sample as stored in said breath storage container is a true alveolar sample;
   said detection means including indicating means responsive to said detection means for indicating visually whether said stored breath sample as stored in said breath storage container has been detected to be a true alveolar sample.

2. A breath collection and storage apparatus as set forth in claim 1 wherein said detection means detects the moisture content in said stored breath sample.

3. A breath collection and storage apparatus as set forth in claim 2 wherein said indicating means is responsive to the moisture content detected by the detection means.

4. A breath collection and storage apparatus as set forth in claim 3 wherein said indicating means changes color in response to the detected moisture content.

5. A breath collection and storage apparatus as set forth in claim 4 wherein said indicating means contains cobalt chloride which changes color in response to the detected moisture content.

6. A breath collection and storage kit comprising:
   a container for collecting and storing a breath sample from a human subject;
   a detector adapted to be positioned within said container for detecting and indicating while positioned within said container whether said stored breath sample as stored in said container is a true alveolar sample; and
   closure means for closing said container with said breath sample and said detector stored together in said container.

7. A breath collection and storage kit as set forth in claim 6 wherein said detector detects the moisture content in said stored breath sample.

8. A breath collection and storage kit as set forth in claim 7 wherein said detector changes color in response to the detected moisture content.

9. A breath collection and storage kit as set forth in claim 8 wherein said detector contains cobalt chloride which changes color in response to the detected moisture content.

10. A method of collecting and storing a human breath sample which comprises the steps of:
    providing a container for collecting and storing said breath sample;
    positioning detection and indicating means within said container in which said breath sample is to be collected and stored;
    collecting and storing said breath sample in said container having said detection and indicating means positioned therein and closing said container;
    detecting by means of said detection and indicating means and while said detection and indicating means is positioned in said closed container whether the sample as stored in said closed container is a true alveolar sample; and
    indicating to an observer by means of said detection and indicating means while said detection and indicating means is positioned in said closed container whether the breath sample as stored in said closed container is a true alveolar sample.

11. A method of collecting and storing a human breath sample as set forth in claim 10 wherein said detection step includes detection of the moisture content of said breath sample in said closed container.

12. A method of collecting and storing a human breath sample as set forth in claim 11 wherein said detecting and indicating steps include displaying a particular color which is indicative of whether said stored breath sample is a true alveolar sample.

13. A method of collecting and storing a human breath sample as set forth in claim 12 wherein said detector contains cobalt chloride which changes color in response to the detected moisture content.

14. A breath sample collection and storage kit for collecting and storing a human breath sample for analysis of the constituent components thereof, comprising:

an elongated, rigid hollow and transparent tubular container having an elongated chamber therein, one end of said container being closed and an opposite end thereof having an inlet portion forming an opening to the interior of said chamber;

a hollow breath delivery means for delivering a breath sample from a subject's mouth, said breath delivery means being insertable into said chamber through said inlet portion to deliver to said chamber a breath sample expelled from said subject's mouth, said chamber having a volume which is substantially less than the volume of a breath sample normally expelled by a human whereby said expulsion of said breath purges said chamber of an initial portion of said breath through said inlet portion leaving only primarily an alveolar portion of the expelled breath;

a closure means for closing and substantially sealing the inlet portion of said tube and said chamber with said breath sample sealed therein; and a detector adapted to be positioned within said chamber and sealed therein with said breath sample for detecting and indicating while said detector is positioned and sealed within said chamber with said stored breath sample whether said stored breath sample as stored in said chamber is a true alveolar sample.

15. A breath collection and storage kit as set forth in claim 14 wherein said detector detects the moisture content in said stored breath sample.

16. A breath collection and storage kit as set forth in claim 15 wherein said detector changes color in response to the detected moisture content.

17. A breath collection and storage kit as set forth in claim 16 wherein said detector contains cobalt chloride which changes color in response to the detected moisture content.

18. A breath collection and storage kit as set forth in claim 17 wherein said detector is a substantially mineral-free base material which has been impregnated with cobalt chloride.

* * * * *